United States Patent
Kasina

(10) Patent No.: US 11,260,064 B2
(45) Date of Patent: Mar. 1, 2022

(54) STABLE CORTICOSTEROID COMPOSITIONS

(71) Applicant: ViroPharma Biologics LLC, Lexington, MA (US)

(72) Inventor: Ramalingeswar Kasina, Lexington, MA (US)

(73) Assignee: VIROPHARMA BIOLOGICS LLC, Lexington, MA (US)

( * ) Notice: Subject to any disclaimer, the term of this patent is extended or adjusted under 35 U.S.C. 154(b) by 0 days.

(21) Appl. No.: 16/244,219

(22) Filed: Jan. 10, 2019

(65) Prior Publication Data

US 2019/0209587 A1    Jul. 11, 2019

Related U.S. Application Data

(60) Provisional application No. 62/616,213, filed on Jan. 11, 2018.

(51) Int. Cl.
*A61K 31/58* (2006.01)
*A61K 47/22* (2006.01)

(52) U.S. Cl.
CPC .............. *A61K 31/58* (2013.01); *A61K 47/22* (2013.01)

(58) Field of Classification Search
CPC ................................ A61K 31/58; A61K 47/22
See application file for complete search history.

(56) References Cited

U.S. PATENT DOCUMENTS

| | | |
|---|---|---|
| 4,830,853 A | 5/1989 | Murthy et al. |
| 5,945,106 A | 8/1999 | Sinnott |
| 2003/0114430 A1 | 6/2003 | MacLeod et al. |
| 2009/0324736 A1 | 12/2009 | Johnson et al. |
| 2016/0166508 A1 | 6/2016 | Pereswetoff-Morath et al. |

FOREIGN PATENT DOCUMENTS

WO    2014155397    10/2014

OTHER PUBLICATIONS

International Search Report and Written Opinion dated May 8, 2019 in connection with PCT International Application No. PCT/US19/12965.
Supplementary European Search Report dated Aug. 20, 2021 in connection with EPO Application No. 19738625.3.
Kumler W.D. et al., "Dissociation Constants of l-Ascorbic Acid and Diethyl Dihydroxymaleate", Journal of the American Chemistry Society, Oct. 1, 1935, p. 1929.

*Primary Examiner* — Sahar Javanmard
(74) *Attorney, Agent, or Firm* — Troutman Pepper Hamilton Sanders LLP

(57) ABSTRACT

The invention relates to pharmaceutical compositions comprising a corticosteroid and an antioxidant. The invention further relates to methods of treating, preventing, or alleviating the symptoms of and inflammation associated with inflammatory diseases and conditions of the gastrointestinal tract comprising administering the pharmaceutical compositions comprising a corticosteroid and an antioxidant.

12 Claims, 1 Drawing Sheet

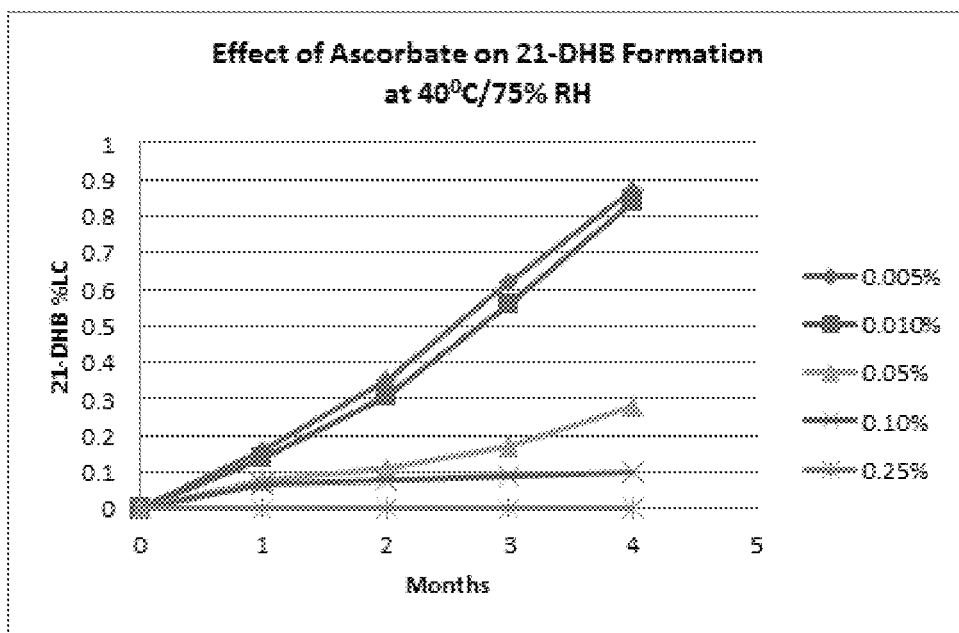

STABLE CORTICOSTEROID COMPOSITIONS

CROSS REFERENCE TO RELATED APPLICATIONS

This patent application claims priority pursuant to 35 U.S.C. § 119(e) to U.S. Provisional Patent Application No. 62/616,213, filed Jan. 11, 2018, which is hereby incorporated by reference in its entirety.

FIELD OF INVENTION

The present invention relates to oxidatively stable pharmaceutical compositions comprising a corticosteroid and an antioxidant.

BACKGROUND OF THE INVENTION

Esophageal inflammation disorders are gaining increased recognition in both adults and children. One example is eosinophilic esophagitis (EE or EoE), which is an emerging, and fast-growing disorder characterized by high levels of eosinophils in the esophagus, as well as basal zone hyperplasia. EE (EoE) is thought to be provoked, in at least a subset of patients, by food allergies or airborne allergen exposure (1-5, 44). EE (EoE) diagnosis is often associated with other hypersensitivity disorders, including asthma, rhinitis, and other food and aeroallergen inhalant sensitivities (39-40). Diagnosis is often made, e.g., in young children and depends on the finding of 15 to 20 or more to 24 or more eosinophils per high power field (eos/hpf) within esophageal mucosal biopsies (6-12).

In parallel with other atopic disorders, the incidence of EE (EoE) appears to be increasing (15, 35). The disorder may present with reflux-like symptoms, pain and dysphagia, clinical symptoms similar to the presentation of gastroesophageal reflux disease ("GERD") (42). Symptoms of EE (EoE) include, for example, abdominal pain, chest pain, choking, difficulty swallowing, failure to thrive, nausea, reflux not relieved by standard anti-flux therapy, skin rash or hives, vomiting, and weight loss. In one series, 15% of EE (EoE) patients had concurrent developmental delay (45).

Although EE (EoE) is becoming more frequently diagnosed throughout developing countries (7, 8, 13-16) many aspects of the disease remain unclear including its etiology, natural history and optimal therapy. Symptoms of EE (EoE) often mimic those of GERD and include vomiting, dysphagia, pain and food impaction (8, 14, 17-20). However, treatment of EE (EoE) and GERD differ and it is important to distinguish between them, particularly as untreated EE (EoE) may be associated with esophageal narrowing in 10-30% of cases (14, 18, 20, 21). The overlap of GERD and EE (EoE) symptoms is common; failure to respond to high PPI GERD treatment may be one diagnostic guideline for EE (EoE) (42). The common occurrence regarding misdiagnosis of EE (EoE) for GERD often results in delayed treatment for patients with EE. (42).

Long term systemic steroid therapy can result in significant secondary side effects on growth and bone development. Although treatment with anti-IL-5 monoclonal antibody has been reported to be successful in EE, this therapy is currently not approved for use in children (36).

Current treatments include elimination diets (22, 23), and elemental formulas (2, 24). Identifying true inciting food allergens can be difficult and elemental formulas are often unpalatable, thereby making dietary interventions complicated (1, 22). Improvised puff and swallow techniques may be difficult for patients, especially smaller children, and especially children with developmental delays, to perform efficiently. This may result in a less than effective dose of a topical steroid being delivered to the esophagus.

Corticosteroid compositions for the treatment of EE have been recently developed, see U.S. Pat. Nos. 8,679,545 and 9,050,368. These compositions are designed for oral administration to the esophagus and comprise a therapeutically active amount of a corticosteroid, along with several excipients.

Oxidative degradation of pharmaceuticals is a problem well known to one of ordinary skill in the art. Corticosteroids, such as budesonide, degrade in the presence of oxygen. Specifically, budesonide is known to undergo oxidative degradation with the formation of the undesirable 21-dehydro budesonide (21-DHB) species upon storage. It is therefore highly desirable to provide pharmaceutical formulations in which an oxidation-susceptible corticosteroid active drug ingredient or ingredients are protected against oxidative degradation inherent to prolonged storage. One way of combatting oxidative degradation is through the use of antioxidants. Some anti-oxidants employed in various pharmaceutical formulations may include, inter alia, vitamin E, ascorbic acid, BHT (butylated hydroxytoluene), BHA (butylated hydroxyanisole), and the like.

A common problem observed on drug product appearance is discoloration of pharmaceutical compositions. There are many potential causes for this issue. For example, the source and manufacturing of raw materials, the composition manufacturing process, and the storage process/conditions. Composition discoloration during storage may involve interaction between active, excipients and packaging materials.

Accordingly, there is a need in the art to provide corticosteroid compositions that do not substantially decompose and/or discolor upon storage. There is further a need in the art to provide corticosteroid compositions that are palatable and do not have bitter taste, and do not cause allergic reactions in most patients.

SUMMARY OF THE INVENTION

Various non-limiting aspects and embodiments of the invention are described below.

In one aspect, a pharmaceutical composition comprising a corticosteroid and an antioxidant is provided, wherein the pharmaceutical composition does not substantially degrade in the presence of oxygen. In one embodiment, the pharmaceutical composition does not substantially show signs of oxidative degradation after one month of storage, or after two months of storage, or after three months of storage, or after four months of storage. In another embodiment, the pharmaceutical composition does not substantially show signs of oxidative degradation after one month of storage, or after two months of storage, or after three months of storage, or after four months of storage, at 40° C. and at 75% humidity. In another embodiment, the corticosteroid is budesonide. In yet another embodiment, the pharmaceutical composition comprises an antioxidant comprising the combination of ascorbic acid and a pharmaceutically acceptable ascorbate salt. In yet another embodiment, the combination of the ascorbic acid and the pharmaceutically acceptable salt of ascorbate is present in an amount of from about 0.01% to about 0.5% w/w of the composition, or from about 0.05% to about 0.25% w/w of the composition.

In yet another embodiment, the pharmaceutical composition may further comprise a viscosity modifying agent, a preservative, a flavoring agent, a sweetener, an at least one additional excipient, and a pharmaceutically acceptable vehicle. In some embodiments, the pharmaceutical composition may discolor after storage, e.g., after one month of storage, or after two months of storage, or after three months of storage, or after four months of storage. In other embodiments, the pharmaceutical composition does not substantially discolor after storage, e.g., after one month of storage, or after two months of storage, or after three months of storage, or after four months of storage. In one embodiment, the pharmaceutical composition has a pH of between about 4 and about 5.2. In another embodiment, the pharmaceutical composition comprises antimicrobial preservatives, such as sodium benzoate and potassium sorbate.

In another aspect, methods for treating, preventing, or alleviating the symptoms of and inflammation associated with inflammatory diseases and conditions of the gastrointestinal tract, e.g., the esophagus, comprising administering a pharmaceutical composition comprising a therapeutically effective amount of a corticosteroid and an antioxidant are provided. In one embodiment, the administered pharmaceutical composition does not substantially degrade in the presence of oxygen. In one embodiment, the pharmaceutical composition is administered orally. In another embodiment, the inflammation of the gastrointestinal tract is inflammation of the esophagus.

In some embodiments, administration of a pharmaceutical composition described herein is to an individual that has been diagnosed with eosinophilic esophagitis, an inflammatory bowel disease involving the esophagus, Crohn's disease, celiac disease, proximal gastrointestinal pathology (e.g., in individuals suffering from hypofunctioning gallbladder), eosinophilic gastrointestinal inflammation, eosinophilic duodenitis, duodenal eosinophilia, functional dyspepsia, intermediate esophagitis, esophageal inflammation secondary to caustic/irritant ingestion, persistent/recurrent esophageal strictures of any cause and including caustic/irritant ingestion, pill-induced esophagitis, systemic diseases, congenital diseases, post-surgery inflammation, intermediate esophagitis, epithelial hyperplasia, basal cell hyperplasia, elongated papillae, dilated vessels in papillae, fungal esophagitis (e.g., *Candida*, turolopsis, *histoplasma Aspergillus*, etc.), viral esophagitis (e.g., HSV, CMV, V2V), bacterial esophagitis (e.g., tuberculosis, actinomycosis, syphlis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behçet's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, or gastro enteritis. In specific embodiments, the individual has eosinophilic esophagitis. In some specific embodiments, the individual has been diagnosed with gastroesophageal reflux disease (GERD), nonerosive reflux disease (NERD), or erosive esophagitis. In some embodiments, the inflammation of the gastrointestinal tract is inflammation of the stomach and/or the small intestines, e.g., gastro enteritis. In one embodiment, the inflammation of the gastrointestinal tract is eosinophilic esophagitis (EE or EoE).

In certain embodiments, the individual administered a pharmaceutical composition for the treatment, prevention or alleviation of inflammation or symptoms associated with inflammation of the gastrointestinal tract is a child or an infant. In various embodiments, the child or infant is less than 16 years old, less than 12 years old, less than 8 years old, less than 6 years old, less than 4 years old or less than 2 years old.

In some embodiments, pharmaceutical dosage forms are provided, the dosage forms comprising a pharmaceutical composition comprising a corticosteroid and an antioxidant (e.g., any pharmaceutical composition described herein). In some embodiments, the pharmaceutical composition of the invention is in liquid form. Liquid forms include, by way of non-limiting example, emulsions, solutions, suspensions, syrups, slurries, dispersions, colloids and the like. In some embodiments, the pharmaceutical composition is in a unit dose formulation for oral administration to a subject. In some embodiments, the pharmaceutical composition is in unit dose packaging, such as a stick-pack (e.g., Unistick®), or a sachet.

In some embodiments, provided herein is a kit comprising a multiple unit container and a plurality of unit doses of a pharmaceutical composition comprising a corticosteroid and an antioxidant (e.g., any pharmaceutical composition described herein).

These and other aspects of the present invention will become apparent to those skilled in the art after a reading of the following detailed description of the invention, including the appended claims.

BRIEF DESCRIPTION OF THE DRAWINGS

FIG. 1 is a graph depicting the effect of various concentrations of the combination of ascorbic acid and sodium ascorbate on 21-dehydrobudesonide (21-DHB) formation at 40° C. and 75% relative humidity simulated storage conditions over several months of storage.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In a preferred embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

Pharmaceutical Compositions and Dosage Forms

The present invention provides pharmaceutical compositions comprising a corticosteroid and an antioxidant. In some embodiments, the pharmaceutical compositions further comprise a pharmaceutically acceptable carrier. These compositions can be prepared in a manner well known in the pharmaceutical art, and can be administered by a variety of routes. The pharmaceutical compositions of the invention can be administered locally or systemically. The term "systemic" as used herein includes parenteral, topical, transdermal, oral, by inhalation/pulmonary, rectal, nasal, buccal, and sublingual administration. In one specific aspect, pharmaceutical composition for oral administration are described.

Pharmaceutical compositions comprising a corticosteroid and an antioxidant of the invention can be prepared in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, injectable solutions, including sterile injectable solutions, and sterile packaged powders.

In some embodiments, the pharmaceutical composition of the invention is in liquid form. Liquid forms include, by way of non-limiting example, emulsions, solutions, suspensions, syrups, slurries, dispersions, colloids and the like. In some embodiments, a pharmaceutical composition described herein is in liquid, semi-solid or solid (e.g., powder) form. In specific embodiments, a pharmaceutical composition described herein is in semi-solid form, e.g., a gel, a gel matrix, a cream, a paste, or the like. In some embodiments, semi-solid forms comprise a liquid vehicle.

In some embodiments, pharmaceutical compositions of the invention can include one or more pharmaceutically acceptable carriers. As used herein the language "pharmaceutically acceptable carrier" is intended to include any and all solvents, excipients, dispersion media, coatings, antibacterial and antifungal agents, isotonic and adsorption delaying agents, and the like, compatible with pharmaceutical administration. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X). Except insofar as any conventional media or agent is incompatible with the active compound, such media can be used in the compositions of the invention. Supplementary active compounds can also be incorporated into the compositions.

In some embodiments, a composition is in a unit dose formulation for oral or other administration to a patient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. In some embodiments, the pharmaceutical composition is in unit dose packaging, such as a stick-pack (e.g., Unistick®), or a sachet. The use of a stick-pack (e.g., Unistick®) further avoids the discoloration problem, to which corticosteroid compositions are prone.

In some embodiments, a composition or unit dosage form described herein is administered as an emulsion, a solution, a suspension, a syrup, a slurry, a dispersion, a colloid, a capsule, a gel capsule, a semi-solid, a solid forma gel, a gel matrix, a cream, a paste, a tablet, a granule, a sachet, a powder, or the like. In certain aspects, about 0.000001 mg to about 2000 mg, about 0.00001 mg to about 1000 mg, or about 0.0001 mg to about 500 mg, about 0.001 mg to about 100 mg, about 0.005 mg to about 20 mg, about 0.01 mg to about 10 mg, about 0.05 mg to about 5 mg, or about 0.1 mg to about 1 mg of corticosteroid per day per dose is administered to an individual.

In some embodiments, the pharmaceutical composition or unit dosage form described herein comprises from about 0.001% to about 5% of antioxidant w/w, or from about 0.005 to about 1% of antioxidant w/w, or from about 0.01 to about 0.5% antioxidant w/w, or from about 0.05% to about 0.25% antioxidant w/w, or about 0.1% antioxidant w/w.

In some embodiments, a pharmaceutical composition is provided, wherein the pharmaceutical composition does not substantially degrade and/or discolor in the presence of oxygen upon storage, the pharmaceutical composition comprising:
  a. a therapeutically effective amount of corticosteroid,
  b. a combination of ascorbic acid and a pharmaceutically acceptable ascorbate salt, c. edetate,
d. citrate,
e. polysorbate 80,
f. a preservative,
g. an optional flavoring agent,
h. an optional sweetener, and
i. a liquid vehicle.

In some embodiments, a pharmaceutical composition is provided, wherein the pharmaceutical composition does not substantially degrade and/or discolor in the presence of oxygen upon storage, the pharmaceutical composition comprising:
 a. budesonide in an amount of about 0.02 mg/mL to about 0.75 mg/mL,
 b. a combination of ascorbic acid and a pharmaceutically acceptable ascorbate salt in an amount of about 0.01 mg/mL to about 2.5 mg/mL,
 c. edetate in an amount of about 0.05 mg/mL to about 25 mg/mL,
 d. citrate in an amount of about 0.1 mg/mL to about 30 mg/mL,
 e. polysorbate 80 in an amount of 0.05 mg/mL to about 1 mg/mL,
 f. a preservative,
 g. a flavoring agent, a sweetener, or a combination thereof, and
 h. an aqueous liquid vehicle.

In some embodiments, a pharmaceutical composition is provided, wherein the pharmaceutical composition does not substantially degrade and/or discolor in the presence of oxygen upon storage, the pharmaceutical composition comprising:
 a. budesonide in an amount of about 0.001% to about 0.1% w/w,
 b. a combination of ascorbic acid and a pharmaceutically acceptable ascorbate salt in an amount of about 0.005% to about 0.25% w/w,
 c. edetate in an amount of about 0.005% to about 1% w/w,
 d. citrate in an amount of about 0.01% to about 1% w/w,
 e. polysorbate 80 in an amount of 0.001% to about 0.01% w/w,
 f. a preservative,
 g. a flavoring agent, a sweetener, or a combination thereof, and
 h. an aqueous liquid vehicle.

In some embodiments, a particular pH is sought to achieve desirable properties of the composition of the invention. In one non-limiting example, wherein the preservative sodium benzoate is used as an antimicrobial preservative in the composition, it has been observed that lower pH of the composition results in higher effectiveness of the preservative. In some embodiments, the composition of the invention has an acidic pH, i.e. a pH less than about 7. In some embodiments, the composition has a pH of between about 3 and about 6, or between about 4 and about 5.2.

The choice of an antioxidant suitable for the present compositions is deliberate and relies on many factors specific to the present formulation, the methods of administration, and the patient group. For example, many subjects suffering from inflammatory diseases and conditions of the gastrointestinal tract, e.g., the esophagus, are prone to allergic reactions. Care must be taken to avoid antioxidants that could provoke allergic reactions in the patients. Additionally, care must be taken to mask unpleasant taste and to result in a palatable formulation, particularly since corticosteroids, such as budesonide, have a bitter taste. Therefore, antioxidants that themselves have an unpleasant taste should be avoided. It has been found that the combination of ascorbic acid and an ascorbate salt is non-allergenic, has a pleasant taste, and affords the desirable effect of protecting the formulation from oxidative degradation.

The present application also includes pharmaceutical kits useful, for example, in treating, preventing, or alleviating the symptoms of and inflammation associated with inflammatory diseases and conditions of the gastrointestinal tract, e.g., the esophagus, which include one or more containers containing a pharmaceutical composition comprising a therapeutically effective amount of a corticosteroid and an antioxidant. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Delivery devices are important not only for delivering the pharmaceutical compositions of the invention, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use indicating that the composition should be used, e.g., orally.

Methods of Treatment

In another aspect, methods for treating, preventing, or alleviating the symptoms of and inflammation associated with inflammatory diseases and conditions of the gastrointestinal tract, e.g., the esophagus, comprising administering a pharmaceutical composition comprising a therapeutically effective amount of a corticosteroid and an antioxidant are provided. In one embodiment, the administered pharmaceutical composition does not substantially degrade in the presence of oxygen. In one embodiment, the pharmaceutical composition is administered orally. In another embodiment, the inflammation of the gastrointestinal tract is inflammation of the esophagus.

In some embodiments, administration of a pharmaceutical composition described herein is to an individual that has been diagnosed with eosinophilic esophagitis, an inflammatory bowel disease involving the esophagus, Crohn's disease, celiac disease, proximal gastrointestinal pathology (e.g., in individuals suffering from hypofunctioning gallbladder), eosinophilic gastrointestinal inflammation, eosinophilic duodenitis, duodenal eosinophilia, functional dyspepsia, intermediate esophagitis, esophageal inflammation secondary to caustic/irritant ingestion, persistent/recurrent esophageal strictures of any cause and including caustic/irritant ingestion, pill-induced esophagitis, systemic diseases, congenital diseases, post-surgery inflammation, intermediate esophagitis, epithelial hyperplasia, basal cell hyperplasia, elongated papillae, dilated vessels in papillae, fungal esophagitis (e.g., Candida, turolopsis, *histoplasma Aspergillus*, etc.), viral esophagitis (e.g., HSV, CMV, V2V), bacterial esophagitis (e.g., tuberculosis, actinomycosis, syphlis), corrosive esophagitis, radiation esophagitis, chemotherapy esophagitis, graft vs. host disease, a skin disease with esophageal involvement (e.g., bullous pemphigoid, pemphigus vulgaris, epidermolysis bollosa, Stevens-Johnson syndrome), Behget's disease, sarcoidosis, idiopathic esophagitis, eosinophilic gastritis, Menetrier's disease, parasitic gastritis, lymphocytic esophagitis, inflammatory bowel disease-associated esophagitis, parasitic gastritis, or gastro enteritis. In specific embodiments, the individual has eosinophilic esophagitis. In some specific embodiments, the individual has been diagnosed with gastroesophageal reflux disease (GERD), nonerosive reflux disease (NERD), or erosive esophagitis. In some embodiments, the inflammation of the gastrointestinal tract is inflammation of the stomach and/or the small intestines, e.g., gastro enteritis. In one embodiment, the inflammation of the gastrointestinal tract is eosinophilic esophagitis (EE or EoE).

In certain embodiments, the individual administered a pharmaceutical composition for the treatment, prevention or alleviation of inflammation or symptoms associated with inflammation of the gastrointestinal tract is a child or an infant. In various embodiments, the child or infant is less than 16 years old, less than 12 years old, less than 8 years old, less than 6 years old, less than 4 years old or less than 2 years old.

EXAMPLES

Example 1: Evaluation of the Antioxidant Effect at Various Concentrations

The effect of ascorbate was evaluated at various concentration levels (0.005% to 0.25% w/w). The stability data from an exemplary composition described herein with and without varying amounts of ascorbate are shown in Table 1 and FIG. 1. A comparison of the budesonide formulations (MB-9 and MB-9 w/ascorbate) is shown in Table 1 below.

TABLE 1

| Component | Function | Composition in % w/w MB-9 | MB-9 w/ascorbate |
|---|---|---|---|
| Budesonide | Active ingredient | 0.001-0.1 | 0.001-0.1 |
| Microcrystalline cellulose and/or Carboxymethylcellulose and/or Carbomer and/or HPMC and/or HEC | Viscosity modifier | 0-10 | 0-10 |
| Maltodextrin | Viscosity | 1-50 | 1-50 |
| Dextrose | Flavoring agent | 1-50 | 1-50 |
| Disodium EDTA | Chelating agent | 0.005-1 | 0.005-1 |
| Citric acid | Buffer | 0.01-1 | 0.01-1 |
| Sodium citrate | Buffer | 0.01-2 | 0.01-2 |
| Polysorbate 80 | Surfactant | 0.001-0.01 | 0.001-0.01 |
| Sodium benzoate | Preservative | 0-1 | 0-1 |
| Cherry flavor | Flavoring agent | optional | optional |
| Ascorbic acid and sodium ascorbate | Anti-oxidant | — | 0.005-0.25 |
| Water, purified | Diluent | q.s. | q.s. |
| Nitrogen[a] | Processing aid | — | — |

[a]Nitrogen is used to blanket the compounding vessels containing budesonide and to purge the headspace of the amber glass bottles in which the drug product is packaged, hence no amount is listed.

A significant reduction of 21-DHB was observed between 0.05% to 0.25% w/w of the combination of ascorbic acid and sodium ascorbate in the formulation as shown in FIG. 1.

There is discoloration (an observed color change) over time in the composition, which may be attributable to the presence of ascorbic acid in the formulation. The rate of color change increases with the increase in level of ascorbic acid and increases in storage temperature. Based on the requirement of a significant reduction in the rate of appearance of 21-DHB and the need to minimize the extent of the color change, the formulation with 0.1% w/w concentration of the combination of ascorbic acid and ascorbate salt was selected to be utilized for further studies.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

REFERENCES

1. Liacouras C A, Ruchelli E. Eosinophilic esophagitis. Curr. Opin. Pediatr. 2004; 16:560-6.
2. Kelly K J, Lazenby A J, Rowe P C, et al. Eosinophilic esophagitis attributed to gastroesophageal reflux: improvement with an amino acid based formula. Gastroenterology 1995; 109: 1503-12.
3. Fogg M I, Ruchelli E, Spergel J M. Pollen and eosinophilic esophagitis. J. Allergy Clin. Immunol. 2003; 112: 796-7.
4. Mishra A, Hogan S P, Brandt E B, Rothenberg M E. An etiological role for aeroallergens and eosinophils in experimental esophagitis. J. Clin. Invest 2001; 107:83-90.
5. Spergel J M, Beausoleil J L, Mascarenhas M, Liacouras C A. The use of skin prick tests and patch tests to identify causative foods in eosinophilic esophagitis. J. Allergy Clin. Immunol. 2002; 109:363-8.
6. Ruchelli E, Wenner W, Voytek T, et al. Severity of esophageal eosinophilia predicts response to conventional gastroesophageal reflux therapy. Pediatr. Dev. Pathol. 1999; 2:15-8.
7. Steiner S J, Gupta S K, Croffie J M, Fitzgerald J F. Correlation between number of eosinophils and reflux index on same day esophageal biopsy and 24 hour esophageal pH monitoring. Am. J. Gastroenterol. 2004; 99:801-5.
8. Orenstein S R, Shalaby T M, Di Lorenzo C, et al. The spectrum of pediatric eosinophilic esophagitis beyond infancy: a clinical series of 30 children. Am. J. Gastroenterol. 2000; 95:1422-30.
9. Rothenberg M E, Mishra A, Collins M H, Putnam P E. Pathogenesis and clinical features of eosinophilic esophagitis. J. Allergy Clin. Immunol. 2001; 108:891-4.
10. Ravelli A M, Villanacci V, Ruzzenenti N, et al. Dilated Intercellular Spaces: A Major Morphological Feature of Esophagitis. J. Pediatr. Gastroenterol. Nut. 2006; 42:510-515.
11. Steiner S J, Kernek K M, Fitzgerald I F. Severity of Basal Cell Hyperplasia Differs in Reflux Versus Eosinophilic Esophagitis. J. Pediatr. Gastroenterol. Nutr. 2006; 42:506-509.
12. Mueller S, Aigner T, Neureiter D, Stoke M. Eosinophil infiltration and degranulation in oesophageal mucosa from adult patients with eosinophilic oesophagitis: a retrospective comparative study on pathologic biopsy. J. Clin. Pathol. 2006; 59:1175-80.

13. Croese J, Fairley S K, Masson J W, et al. Clinical and endoscopic features of eosinophilic esophagitis in adults. Gastrointest. Endosc. 2003; 58:516-22.
14. Aceves S, Newbury, R O, Dohil R, Schwimrner J, Bastian J. Distinguishing Eosinophilic Esophagitis in pediatric patients: clinical, endoscopic, and histologic features of an emerging disorder. Journal of Clinical Gastroenterology 2006; 41(3):252-6.
15. Straumann A, Simon H U. Eosinophilic esophagitis: escalating epidemiology? J. Allergy Clin. Immunol. 2005; 115:418-9.
16. Cherian S, Smith N M, Forbes D A. Rapidly increasing prevalence of eosinophilic oesophagitis in Western Australia. Arch. Dis. Child 2006; 91:1000-4.
17. Sant'Anna A M, Rolland S, Fournet J C, et al. Eosinophilic Esophagitis in Children: Symptoms, Histology and pH Probe Results. J. Pediatr. Gastroenterol. Nutr. 2004; 39:373-377.
18. Potter J W, Saeian K, Staff D, et al. Eosinophilic esophagitis in adults: an emerging problem with unique esophageal features. Gastrointest. Endosc. 2004; 59:355-61.
19. Parfitt J R, Gregor J C, Suskin N G, et al. Eosinophilic esophagitis in adults: distinguishing features from gastroesophageal reflux disease: a study of 41 patients. Mod. Pathol. 2006; 19:90-6.
20. Desai T K, Stecevic V, Chang C H, et al. Association of eosinophilic inflammation with esophageal food impaction in adults. Gastrointest. Endosc. 2005; 61:795-801.
21. Straurnann A, Spichtin H P, Grize L, et al. Natural history of primary eosinophilic esophagitis: a follow-up of 30 adult patients for up to 11.5 years. Gastroenterology 2003; 125:1660-9.
22. Spergel J M, Andrews T, Brown-Whitehorn T F, et al. Treatment of eosinophilic esophagitis with specific food elimination diet directed by a combination of skin prick and patch tests. Ann. Allergy Asthma Immunol. 2005; 95:336-43.
23. Kagalwalla A F, Sentongo T A, Ritz S, et al. Effect of six-food elimination diet on clinical and histologic outcomes in eosinophilic esophagitis. Clin. Gastroenterol. Hepatol. 2006; 4:1097-102.
24. Markowitz J E, Spergel J M, Ruchelli E, Liacouras C A. Elemental diet is an effective treatment for eosinophilic esophagitis in children and adolescents. Am. J. Gastroenterol. 2003; 98:777-82.
25. Liacouras C A, Wenner W J, Brown K, Ruchelli E. Primary eosinophilic esophagitis in children: successful treatment with oral corticosteroids. J. Pediatr. Gastroenterol. Nutr. 1998; 26:380-5.
26. Teitelbaum J E, Fox V L, Twarog F J, et al. Eosinophilic esophagitis in children: immunopathological analysis and response to fluticasone propionate. Gastroenterology 2002; 122:1216-25.
27. Faubion W A, Jr., Perrault J, Burgart L J, et al. Treatment of eosinophilic esophagitis with inhaled corticosteroids. J. Pediatr. Gastroenterol. Nutr. 1998; 27:90-3.
28. Aceves S, Dohil R., Newbury R 0, Bastian J F. Topical viscous budesonide suspension for treatment of eosinophilic esophagitis. J. Allergy Clin. Immunol. 2005; 116: 705-6.
29. Noel R J, Putnam P E, Collins M H, et al. Clinical and immunopathologic effects of swallowed fluticasone for eosinophilic esophagitis. Clin. Gastroenterol. Hepatol. 2004; 2:568-75.
30. Remedios M, Campbell C, Jones D M, Kerlin P. Eosinophilic esophagitis in adults: clinical, endoscopic, histologic findings, and response to treatment with fluticasone propionate. Gastrointest. Endosc. 2006; 63:3-12.
31. Dohil R, Newbury R 0, Sellers Z M, et al. The evaluation and treatment of gastrointestinal disease in children with cystinosis receiving cysteamine. J. Pediatr. 2003; 14:224-30.
32. Cheung K M, Oliver M R, Cameron D J, et al. Esophageal eosinophilia in children with dysphagia. J. Pediatr. Gastroenterol. Nutr. 2003; 37:498-503.
33. Fox V L, Nurko S, Furuta G T. Eosinophilic esophagitis: it's not just kid's stuff. Gastrointest. Endosc. 2002; 56:260-70
34. Budin C, Villard-Truc F, Rivet C, et al. [Eosinophilic esophagitis: 3 case reports]. Gastroenterol. Clin. Biol. 2005; 29:73-5.
35. Noel R J, Putnam P E, Rothenberg M E. Eosinophilic esophagitis. N. Engl. J. Med. 2004; 351:940-1.
36. Guajardo J R, Plotnick L M, Fende J M, et al. Eosinophil-associated gastrointestinal disorders: a world-wide-web based registry. J. Pediatr. 2002; 141:576-81.
37. Liacouras C A, Spergel J M, Ruchelli E, et al. Eosinophilic esophagitis: a 10-year experience in 381 children. Clin. Gastroenterol. Hepatol. 2005; 3:1198-206.
38. Liacouras C A. Eosinophilic esophagitis: treatment in 2005. Curr. Opin. Gastroenterol. 2006; 22:147-152.
39. Spergel I M. Eosinophilic esophagitis in adults and children: evidence for a food allergy component in many patients. Curr. Opin. Allergy Clin. Immunol. 2007; 7:274-8.
40. Plaza-Martin, A M, Jimenez-Feijoo R, Andaluz C, Giner-Munoz M T, Martin-Mateos M A, Piquer-Gibert M, Sierra-Martinez J I. Polysensitization to aeroallergens and food in eosinophilic esophagitis in a pediatric population. Alergol. Immunopathol. 2007; 35:35-7.
41. Nicolazzo, J A, Reed, B L, Finnin, B C. Buccal penetration enhancers—how do they really work? J. Controlled Release 2005; 105:1-15.
42. Furuta, G T, Liacouras, C A, Collins, M H, Sandeep, K G, Justinich, C, Putnam, P E, Bonis, P, Hassan, E, Straumann, A, Rothenberg, M E. Eosiniophilic esophagitis in children and adults: A systematic review and consensus recommendations for diagnosis and treatment. Gastroenterology 2007; 133:1342-1363.
43. Aceves, S S, Bastian J F, Newbury, R O, Dohil, R. Oral viscous budesonide: A potential new therapy for eosinophilic esophagitis. Amer. Journal of Gastroenterology 2007; 102:1-9.
44. Rothenberg M E. Eosinophilic gastrointestinal disorders. J. Allergy Clin. Immunol. 2004; 113:11-28.
45. Garrett J K, Jameson S C, Thomson B, Collins M H, Wagoner L E, Freese, D K, et al. Anti-interleukin-5 (mepolizumab) therapy for hypereosinophilic syndromes. J. Allergy Clin. Immunol. 2004; 113:115-9.

What is claimed is:

1. A pharmaceutical composition comprising budesonide, an antioxidant in an amount of from about 0.05% to about 0.5% w/w of the composition, wherein the antioxidant comprises a combination of ascorbic acid and a pharmaceutically acceptable salt of ascorbate, and a flavoring agent, a sweetener, or a combination thereof, wherein the pharmaceutical composition comprises less than 0.3% impurities formed by oxidative degradation, and wherein the pharmaceutical composition is for oral administration.

2. The pharmaceutical composition of claim 1, wherein the composition comprises less than 0.3% impurities formed by oxidative degradation after one month of storage.

3. The pharmaceutical composition of claim 2, wherein the composition does not discolor after one month of storage.

4. The pharmaceutical composition of claim 1, wherein the composition comprises less than 0.3% impurities formed by oxidative degradation and does not discolor after two months of storage.

5. The pharmaceutical composition of claim 1, wherein the composition comprises less than 0.3% impurities formed by oxidative degradation and does not discolor after three months of storage.

6. The pharmaceutical composition of claim 1, wherein after two months of storage the composition comprises less than 0.2% impurities formed by oxidative degradation.

7. The pharmaceutical composition of claim 2, wherein the impurities formed by oxidative degradation comprise 21-dehydrobudesonide.

8. The pharmaceutical composition of claim 1 having a pH of between about 4 and about 5.2.

9. The pharmaceutical composition of claim 1, further comprising a preservative.

10. The pharmaceutical composition of claim 9, wherein the preservative is selected from sodium benzoate and potassium sorbate.

11. The pharmaceutical composition of claim 1, wherein the combination of the ascorbic acid and the salt of ascorbate is present in an amount of from about 0.1% to about 0.5% w/w of the composition.

12. A kit for treating or alleviating the symptoms of and inflammation associated with inflammatory diseases and conditions of the gastrointestinal tract in a subject in need thereof, comprising a pharmaceutical composition comprising budesonide, an antioxidant in an amount of from about 0.05% to about 0.5% w/w of the composition, wherein the antioxidant comprises a combination of ascorbic acid and a pharmaceutically acceptable salt of ascorbate, and a flavoring agent, a sweetener, or a combination thereof, wherein the pharmaceutical composition comprises less than 0.3% impurities formed by oxidative degradation, and wherein the pharmaceutical composition is for oral administration.

* * * * *